(12) United States Patent
Brockmann et al.

(10) Patent No.: US 12,268,434 B2
(45) Date of Patent: *Apr. 8, 2025

(54) ELECTRODE INSTRUMENT FOR A RESECTOSCOPE, AND RESECTOSCOPE

(71) Applicant: Olympus Winter & Ibe GmbH, Hamburg (DE)

(72) Inventors: Christian Brockmann, Hollenstedt (DE); Christoph Knopf, Stockelsdorf (DE); Andreas Offt, Reinbek (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 411 days.

This patent is subject to a terminal disclaimer.

(21) Appl. No.: 17/665,789

(22) Filed: Feb. 7, 2022

(65) Prior Publication Data
US 2022/0249153 A1   Aug. 11, 2022

(30) Foreign Application Priority Data
Feb. 5, 2021   (DE) .................. 10 2021 102 736.5

(51) Int. Cl.
*A61B 18/14* (2006.01)
*A61B 18/00* (2006.01)

(52) U.S. Cl.
CPC .. *A61B 18/149* (2013.01); *A61B 2018/00077* (2013.01); *A61B 2018/00083* (2013.01); *A61B 2018/00601* (2013.01); *A61B 2018/00982* (2013.01); *A61B 2018/1407* (2013.01); *A61B 2218/002* (2013.01)

(58) Field of Classification Search
CPC ........ A61B 18/149; A61B 2018/00601; A61B 2018/1407; A61B 2018/00982; A61B 18/1485
See application file for complete search history.

(56) References Cited

U.S. PATENT DOCUMENTS

| | | | | |
|---|---|---|---|---|
| 3,939,839 A | * | 2/1976 | Curtiss ................. | A61B 18/149 600/105 |
| 4,726,370 A | * | 2/1988 | Karasawa .............. | A61B 18/14 600/105 |
| 6,113,597 A | * | 9/2000 | Eggers ................... | A61B 18/12 606/41 |

(Continued)

FOREIGN PATENT DOCUMENTS

| | | |
|---|---|---|
| DE | 199 10 295 A1 | 9/2000 |
| DE | 102 48 839 A1 | 5/2004 |

(Continued)

*Primary Examiner* — Jaymi E Della
(74) *Attorney, Agent, or Firm* — Oliff PLC

(57) ABSTRACT

Radiofrequency instruments such as the resectoscope described here are used in medicine for treating body tissue and in particular for removing or manipulating this tissue. A particular disadvantage of the known instruments is that an irrigation liquid is disturbed by an electrode instrument in such a way that the resulting turbulence limits the view of the operator. The invention makes available an electrode instrument by which this problem is solved. This is achieved by the fact that two electrode casing tubes run from an electrode to the proximal end region of the electrode instrument and each have a respective electrical contact, namely an active contact and a return contact.

13 Claims, 3 Drawing Sheets

(56) References Cited

U.S. PATENT DOCUMENTS

| | | | | |
|---|---|---|---|---|
| 6,152,921 A * | 11/2000 | Gminder | ............... | A61B 18/149 |
| | | | | 606/46 |
| 2012/0203221 A1* | 8/2012 | Van Wyk | ............ | A61B 18/1482 |
| | | | | 606/41 |
| 2014/0236143 A1* | 8/2014 | Ward | ................. | A61B 18/1442 |
| | | | | 606/39 |
| 2015/0066018 A1* | 3/2015 | Doll | .................... | A61B 18/1206 |
| | | | | 606/39 |
| 2016/0317213 A1* | 11/2016 | Wolter | ................. | A61B 18/149 |

FOREIGN PATENT DOCUMENTS

| | | |
|---|---|---|
| DE | 102 58 730 A1 | 7/2004 |
| DE | 10 2013 109 505 A1 | 3/2015 |
| DE | 10 2018 127 919 A1 | 5/2020 |
| JP | H10-295701 A | 11/1998 |

* cited by examiner

ELECTRODE INSTRUMENT FOR A RESECTOSCOPE, AND RESECTOSCOPE

The invention relates to an electrode instrument for a resectoscope and a resectoscope.

Radiofrequency instruments such as the resectoscope described here are used in medicine for treating body tissue and in particular for removing or manipulating this tissue. Typical uses are those in urology. One example that may be mentioned is resection of the prostate. A radiofrequency tool used in a resectoscope can be an electrode or an RF electrode, which is attached to a radiofrequency generator, the generator being able to be activated and deactivated with a switch by an operator. The radiofrequency current has the effect that a plasma forms at the electrode. On account of the thermal energy introduced and the interaction of the plasma with the tissue, these RF electrodes are particularly well suited for the treatment of tissue.

For manipulating the tissue, the electrode can be embodied as a cutting loop or as a button electrode, but also as a needle, roller, band, etc., and, with the radiofrequency voltage switched on, can be guided very easily and almost without resistance through the body tissue that is to be removed. In addition to the cutting of body tissue, the tissue can also be manipulated in another way. For this purpose, provision is made that different radiofrequency tools or different electrodes are used for the treatment.

The electrode is latched releasably to a working element of the resectoscope via an electrode instrument. During the treatment of the body tissue, the electrode instrument is moved with the electrode along a longitudinal direction of the resectoscope. Depending on whether the resectoscope is an active or passive resectoscope, the working element or the carriage is connected, by a compression spring or a tension spring, to a main body that has a grip unit.

Known electrode instruments have a forked basic shape. Two fork tubes each carry, at the distal end, an end of the electrode. These fork tubes are brought together in the direction of the proximal end and lead into a common electrode casing tube. In this embodiment of an electrode instrument, the active current path or the active contact of the electrode is routed through the interior of the electrode casing tube, while the return of the current path or of the return contacts is effected via the outer casing of the casing tube. The forked design of the electrode instrument is usually provided in the distal end region of the resectoscope.

In addition to the electrode instrument, it is also conceivable that further components, for example an optical unit, are routed through the working element. This optical unit can be designed as a rod lens system or as an optical waveguide, allowing the operator to view the treatment site inside the body by means of a camera or directly through an eyepiece during the operation. Particularly when using the electrode, it is extremely important that the operator has an unrestricted view of the cutting procedure. Accordingly, a distal end of the optical unit is oriented in such a way that the field of view of the operator is directed directly to the electrode and the movement of the electrode is coupled to the movement of the optical unit.

During the cutting of the tissue, the view of the operator can be clouded by developing gas bubbles and by bleeding. To counteract this, the region in front of the distal end of the resectoscope is flushed clear by an irrigation liquid. The liquid is for this purpose conveyed through the shaft of the resectoscope and emerges at the distal end. For a clear view, it is essential that the emerging irrigation liquid has as far as possible a laminar behavior. An optimized flow can be achieved in particular if the flow of the irrigation liquid is not disturbed at the outlet end, i.e. at the distal end of the resectoscope.

Such a disturbance can be caused, however, by the forked design of the electrode instrument. The liquid flowing through the shaft impinges on the fork and starts swirling. This swirling of the irrigation liquid leads to a turbulent flow, which is particularly disadvantageous for the operator's view. Relocating the fork along the electrode instrument would have the effect that the latter would no longer have the necessary mechanical stability. Overall, the forked basic shape is needed in order to connect the electrode to the current-carrying contacts and to the working element.

The object of the invention is to make available an electrode instrument and a resectoscope by which the above-mentioned problems are solved.

This object is achieved by the exemplary embodiments disclosed in this application. Accordingly, provision is made that two electrode casing tubes run from an electrode to the proximal end region of the electrode instrument and each have a respective electrical contact, namely an active contact and a return contact. By means of these two continuous electrode casing tubes, it is possible to dispense with a forked design of the electrode casing tubes. A swirling motion of an irrigation liquid that flows from a proximal end to a distal end of the electrode instrument along the electrode casing tubes is thereby avoided.

Furthermore, provision can preferably be made that the active contact or the corresponding electrical conductor is arranged electrically insulated inside an electrode casing tube, and the return contact or the corresponding electrical conductor is formed by the outer casing of the electrode casing tube or is conductively connected to the casing of at least one electrode casing tube. Through this division of the two contacts, the current carrying in the electrode instrument can be made particularly simple, efficient and safe.

The electrical contacting inside the working element is also facilitated by this current carrying.

It is furthermore conceivable that the active contact protrudes from one of the two electrode casing tubes for the electrical contacting of the electrode at the proximal end of the electrode instrument or that at least one contact face of the active contact is freely accessible outside the electrode casing tube. The electrical conductor, which forms the active contact, can preferably also be routed through the corresponding other electrode casing tube, said conductor ending there at least a few centimeters in front of the proximal end of the electrode casing tube.

In addition, provision is made according to the invention that at least distal and proximal portions of the electrode casing tubes run parallel to each other, wherein preferably the electrode casing tubes run parallel to each other along their entire length. Accordingly, the electrode casing tubes are also oriented parallel to the resectoscope or the shaft and the optical unit. This parallel orientation of the electrode casing tubes, and in particular of all the components, results in an optimized flow of the irrigation liquid. This parallelism of the electrode casing tubes thus results in a particularly clear view of the treatment site.

It is also conceivable according to the invention that longitudinal axes of proximal and distal portions of one of the electrode casing tubes lie in a common first plane, and longitudinal axes of proximal and distal portions of the other electrode casing tube lie in a common second plane. The first plane and the second plane are oriented parallel to each other and therefore have the same distance from each other along the entire length of the electrode casing tubes. The proximal portions are therefore not offset relative to the distal portions, which offset would lead to a disturbance of the flow of irrigation liquid. Instead, this parallelism of the portions means that said portions of the electrode casing tubes are routed rectilinearly along the entire length of the electrode instrument. This geometry is able to create optimal conditions for a flow that is at least almost free of disturbance.

In a further preferred illustrative embodiment of the invention, the proximal portions of the electrode casing tubes, in particular the active contact and the return contact, are of a rectilinear configuration along a length of at least 24 mm, preferably at least 40 mm. The contacting between the electrode instrument and the working element is particularly advantageous and simple on account of this rectilinear configuration of the end portions. This dimensioning allows this electrode instrument to be coupled to and uncoupled from the working element in a particularly simple manner. A further advantage over existing systems is that a flexible region can be dispensed with by virtue of the long rectilinear portion. In this way, the actuating force is reduced, since less force has to be applied for elastic deformation. In addition, no transverse forces act on seals. Moreover, it permits a greater axial region on which the electrode can be contacted in the carriage.

Particularly preferably, provision can be made that the distal portions of the electrode casing tubes are of a rectilinear configuration along a length of at least 100 mm, preferably at least 200 mm. This rectilinear configuration of the distal portions leads optimally to a laminar flow of the irrigation liquid inside the shaft. By virtue of this rectilinear and parallel routing of the electrode casing tubes at least along the entire length of the distal end portion, the flow behavior of the irrigation liquid is virtually undisturbed, as a result of which swirling in front of the optical unit is suppressed.

Preferably, the invention further provides that distal longitudinal axes of distal portions of the electrode casing tubes each have at least one offset in relation to proximal longitudinal axes of proximal portions of the electrode casing tubes. This offset of the longitudinal axes along the longitudinal axis of the resectoscope can be designed as an S-shape for example along a length of at most 30 mm, preferably 15 mm. Through this offset of the proximal and distal portions, the electrode is supported and positioned particularly advantageously and at the same time the electrical contacts at the proximal end of the electrode instrument are brought into an advantageous position for coupling them to the working element. The offsets tend to be arranged more in the direction of the proximal end of the electrode instrument, so as to minimize the influence on the flow profile at the distal end.

In a particularly advantageous embodiment of the invention, the offset measures 2.5 mm to 3.5 mm, in particular 2.7 mm to 3.1 mm, in particular 2.9 mm. It has been found that such an offset is particularly advantageous for the electrical contacting and the mechanical stability, but also for a laminar flow of the irrigation liquid.

In particular, provision can be made according to the invention that the distance between the electrode casing tubes in the proximal region measures 5.4 mm to 5.8 mm, preferably 5.6 mm, and/or the distance between the electrode casing tubes in the distal region measures 5.4 mm to 5.8 mm, preferably 5.6 mm. This spacing of the electrode casing tubes results, on the one hand, in particularly efficient utilization of the space in the shaft of the resectoscope, while on the other hand sufficient space remains available in the interior of the shaft for the irrigation liquid and other components such as the optical unit. Furthermore, an advantage of the spacing in the distal portion is that it is possible to position the electrode casing tubes between inner shaft and outer shaft. A spacing in the proximal portion has the advantage that, in addition to the offset, the distance to the optical unit can be increased in order to create space for the contacting in the carriage. An equal spacing of the distal and proximal portions also has the advantage that the production of the electrode instrument is simplified, since the electrode casing tubes have to be pivoted only in one spatial direction.

A further essential feature of the invention can be that the diameter of the electrode casing tubes measures 1 mm to 1.4 mm, preferably 1.2 mm, wherein a cross section of the electrode casing tubes is circular or ring-like at least in some regions, preferably along the entire length of the electrode casing tubes. This dimensioning of the casing tubes is particularly advantageous since it provides sufficient mechanical stability along the entire length of the instrument. Furthermore, this dimensioning is sufficient to supply the cutting electrode with the corresponding electrical energy. With this dimensioning, it is furthermore possible to position the electrode casing tubes between inner shaft and outer shaft, specifically with optimal weighing-up between flow cross sections and the manufacturability of the mechanical components of the resectoscope. Moreover, with such dimensioning, the electrode instrument can be particularly easily handled by the operator, in particular coupled to and uncoupled from the working element. It is particularly advantageous that the sealing takes place at the greatest diameter. No larger element has to be routed through the seal in the working element. In particular, the crimping of the electrode casing tubes can be carried out to deviate only slightly from the circular cross-sectional shape, in order not to influence the flow behavior of the irrigation liquid.

It is furthermore conceivable that all the components of the electrode, in particular of the return contact, in the proximal region are located within an extended, enveloping cylinder face of the casing tubes and do not protrude radially beyond same.

In addition, an advantageous development of the present invention can be one in which the electrode casing tubes are connected via at least one guide element or guide plate, in particular two guide elements, in the distal portion, preferably via a first guide element in the distal portion and a second guide element in the proximal portion. A web-like guide element of this kind connects the two electrode casing tubes such that their relative position remains at least substantially constant, even under the action of a mechanical force. In addition, provision can be made that a cross section of the at least one guide element is curved or forms a segment of a circle, such that the guide element adapts to the inner wall of the outer shaft, the outer wall of the optical unit or the inner/outer wall of the inner shaft or optical unit. The guide element of the electrode instrument fixes the latter in such a way that the electrode instrument is only movable in the axial direction of the shaft/optical unit.

The guide element is designed in such a way that the flow of the irrigation liquid is disturbed as little as possible. For this purpose, the guide element is offset from the inflow to the outflow. The ends of the at least one guide element are fixedly connected to the outer casing of the electrode casing tubes. The ends of the guide elements can be fixedly connected to the casing tubes, namely either adhesively bonded, welded, crimped, soldered, latched or the like. The guide elements are preferably metallic. However, they can equally be produced also from a plastic or a composite material.

The object mentioned at the outset is further achieved by the exemplary embodiments disclosed in this application. Accordingly, provision is made that a resectoscope has an electrode instrument as described in this application. By means of such resectoscopes, the treatment region can be reliably supplied with an RF plasma and can also be clearly viewed as a result of an irrigation liquid having an as far as possible laminar flow.

A preferred illustrative embodiment of an electrode instrument is described in more detail below with reference to the drawing, in which.

Figure 1:
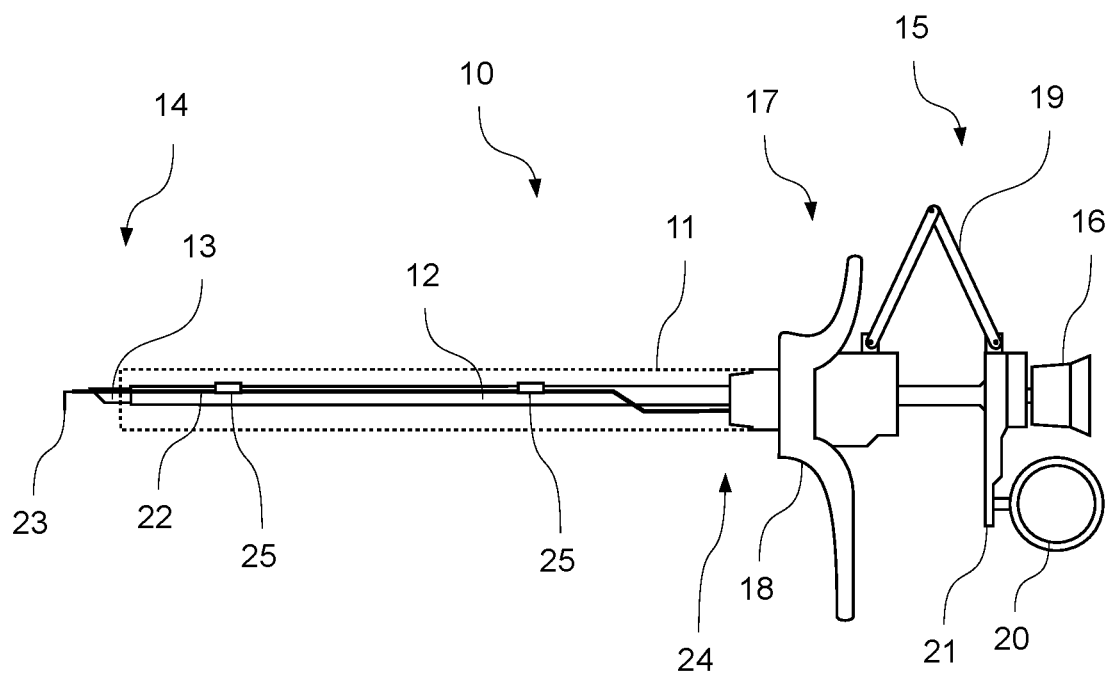
FIG. 1 shows a schematic view of a resectoscope.

FIG. 1 shows a possible illustrative embodiment of a resectoscope 10. In this resectoscope 10, an outer shaft 11, only symbolized here by dashed lines, is pushed over an inner shaft 12. The inner shaft 12 serves to receive and/or guide an optical unit 13, which extends from a distal end 14 to a proximal end 15 of the resectoscope 10. At the proximal end 15, an eyepiece 16 is available to allow a user to observe, through the optical unit 13, the region in which surgery is to be performed in front of the distal end 14.

An essential component of the resectoscope 10 is the working element 17. his working element 17 has a first gripping means 18, among other things, and is connected by a spring element 19 to a second gripping means 20 and to an optical plate 21.

Moreover, an electrode instrument 22 extends along the inner shaft 12 from the distal end 14 of the resectoscope 10 as far as the working element 17. At the distal end 14, the electrode instrument 22 has an electrode 23. Electrical energy is able to be applied to this electrode 23 by means of an RF generator (not shown) and serves to manipulate tissue.

The electrode instrument 22 is latched with a proximal end 24 in the working element 17. In this way, on the one hand, the electrode instrument 22 can be easily uncoupled from the working element 17 or coupled to the working element 17 and, on the other hand, can move together with the working element 17 along the longitudinal axis of the resectoscope 10 in the distal or proximal direction.

Figure 2:
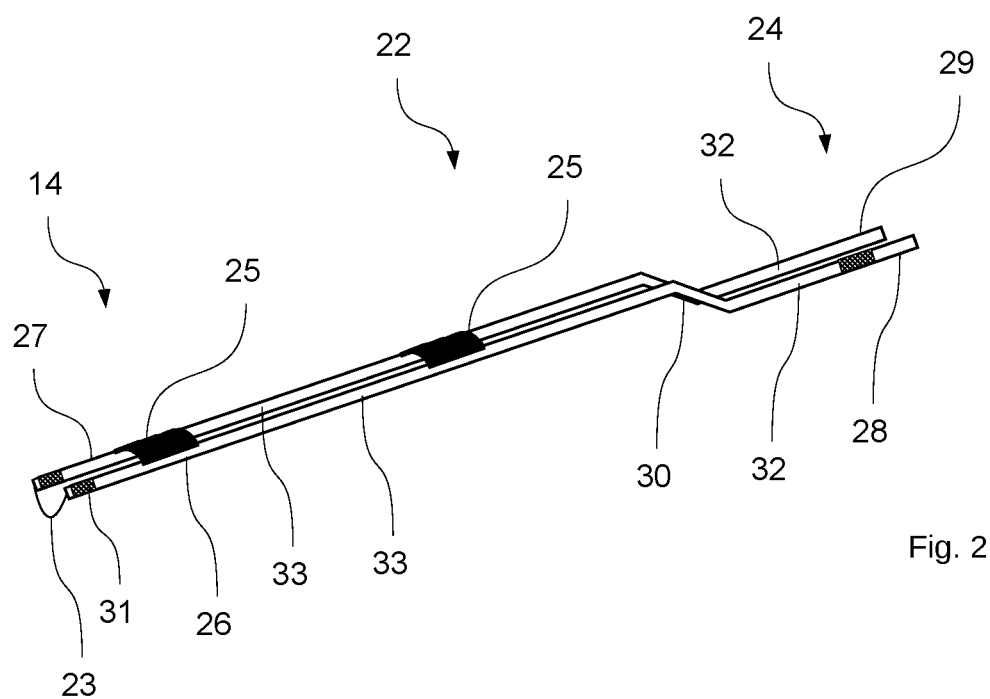
FIG. 2 shows a schematic, perspective view of an electrode instrument.

According to the invention, the electrode instrument 22 shown in FIG. 2 has two electrode casing tubes 26, 27. These electrode casing tubes 26, 27 are substantially rectilinear. The electrode casing tubes 26, 27 run parallel to each other along their entire length, i.e. from the distal end 14 to the proximal end 24. The distance between the electrode casing tubes 26, 27 measures between 5.4 mm and 5.8 mm, preferably 5.6 mm. At the distal ends, the two electrode casing tubes 26, 27 are mechanically connected to each other by the electrode 23 and electrically insulated from each other by the insulator 31. When an RF voltage is applied to the electrode instrument 22, a plasma forms around the electrode 23, designed here as a cutting loop. The electrical contacting of the electrode instrument 22 takes place via the two proximal ends of the electrode casing tubes 26, 27. While an active contact 28 insulated in the interior of the electrode casing tube 26 runs from the proximal end 24 to the electrode 23, an outer casing of the electrode casing tube 27 forms a return contact 29. As has already been described, these two contacts 28, 29 are plugged into the working element 17 and electrically connected by corresponding lines to the RF generator (not shown here).

The electrode casing tubes 26, 27 deviate from their rectilinear shape to the extent that proximal portions 32 each have an offset 30 with respect to distal portions 33. As a result of this offset 30, longitudinal axes of the proximal portions 32 and of the distal portions 33 of the individual electrode casing tubes 26, 27 are displaced parallel to each other, wherein the proximal portion 32 and the distal portion 33 of the electrode casing tube 26 lie in a first plane, which is oriented parallel to a second plane formed by the proximal portion 32 and the distal portion 33 of the electrode casing tube 27. The offset 30 between the displaced longitudinal axes can measure 2.5 mm to 3.5 mm, others 2.7 mm to 3.1 mm, preferably 2.9 mm. This offset 30 can be step-like or also S-shaped.

Figure 3:
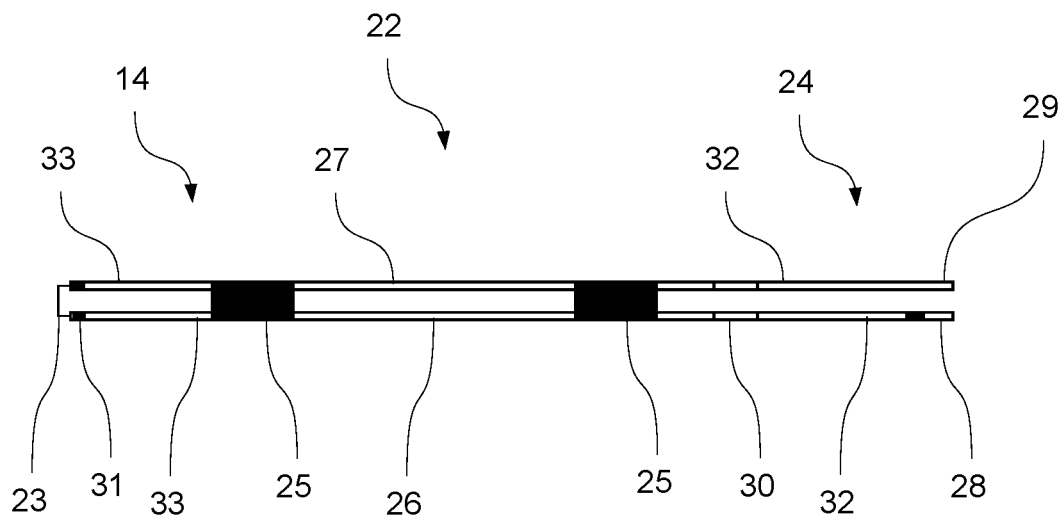
FIG. 3 shows a view of the electrode instrument according to FIG. 2.
Figure 4:
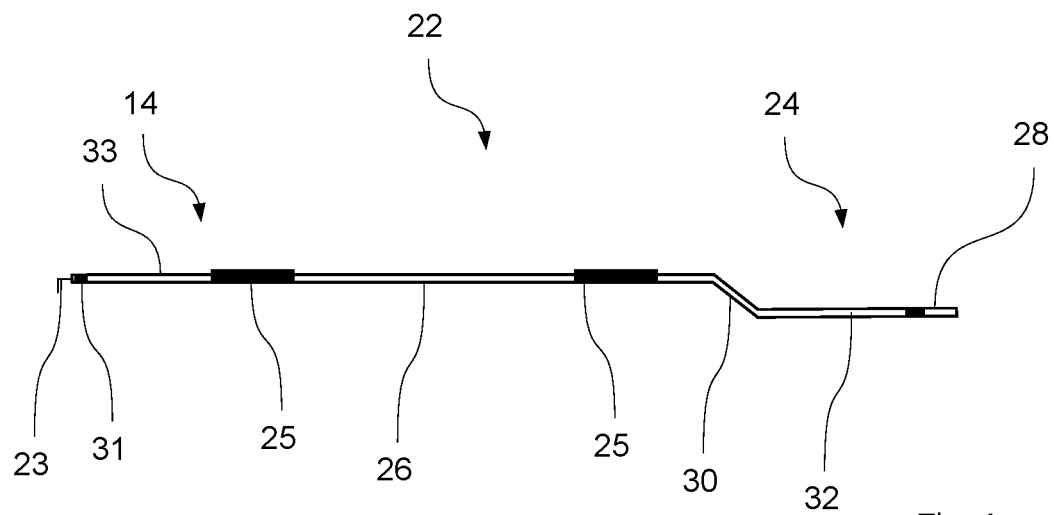
FIG. 4 shows a side view of the electrode instrument according to FIG. 2.
Figure 5:
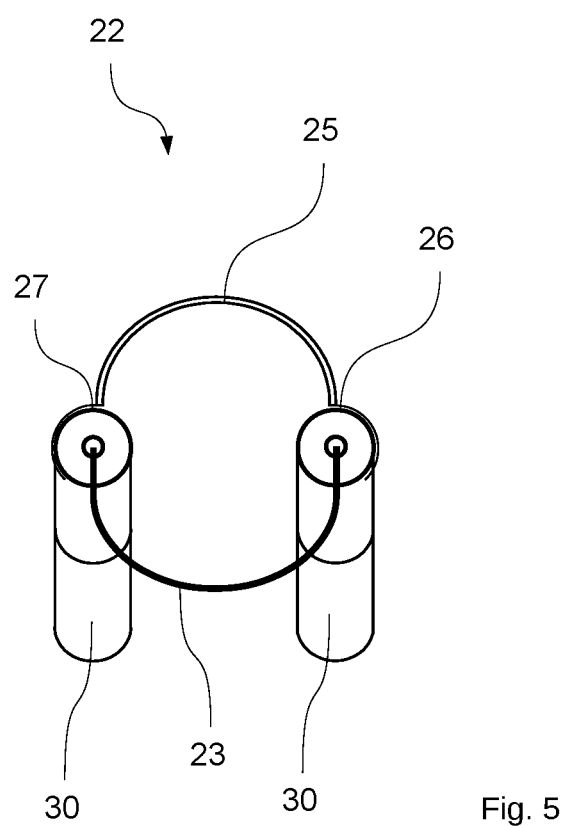
FIG. 5 shows a view of a distal end of the electrode instrument according to FIG. 2.

In the illustrative embodiment of the electrode instrument 22 shown in FIGS. 2-4, provision is made that the distal rectilinear portion 33 of the electrode casing tubes 26, 27 has at least a length of 100 mm, preferably of 200 mm. By virtue of this design at least of the distal portion 33 of the electrode casing tubes 26, 27, there is a particularly advantageous laminar flow of the irrigation liquid in the shaft 11. The rectilinear proximal portion 32 of the electrode casing tubes 26, 27 preferably has a length of 24 mm, preferably 40 mm. This dimensioning allows the contacts 28, 29 to be particularly easily and safely handled and coupled to the working element 17. For additional mechanical stability, the two electrode casing tubes 26, 27 can be coupled to each other via guide elements 25, as is shown in FIGS. 2 and 3. These guide elements 25 serve for mechanically stabilizing the electrode casing tubes 26, 27 relative to each other, but especially also for guiding the electrode instrument 22 on the inner shaft 12. During use of the resectoscope 10, the guide elements 25 lie on an outer jacket surface of the inner shaft 12 and slide with corresponding movement along the shaft axis. It can be seen from FIG. 5 that the cross section of the guide elements 25 is in the shape of a segment of a circle and can thus particularly advantageously conform to the outer shape of the inner shaft 12. It can also be seen from FIG. 5 that the guide elements 25 are fastened with their edge regions to the electrode casing tubes 26, 27, or these edge regions extend at least partially around the electrode casing tubes 26, 27. These guide elements 25 can be produced either from a metallic material or alternatively from a plastic or composite material. On account of the positioning of the guide elements 25 above the inner shaft 12, the irrigation liquid flowing through the shaft 11 remains unaffected by these plates 25.

In order to optimally utilize the limited interior space of the shaft 11, the diameter of the electrode casing tubes 26, 27 measures 1.0 mm to 1.4 mm, preferably 1.2 mm.

In addition to the resectoscope 10 shown here as an example, it is also conceivable for the electrode instrument 22 according to the invention to be connected to a resectoscope of a different configuration.

| List of reference signs | |
| --- | --- |
| 10 | resectoscope |
| 11 | outer shaft |
| 12 | inner shaft |
| 13 | optical unit |
| 14 | distal end of resectoscope |
| 15 | proximal end of resectoscope |
| 16 | eyepiece |
| 17 | working element |

-continued

| | List of reference signs |
|---|---|
| 18 | gripping means |
| 19 | spring element |
| 20 | gripping means |
| 21 | optical plate |
| 22 | electrode instrument |
| 23 | electrode |
| 24 | proximal end of electrode instrument |
| 25 | guide element |
| 26 | electrode casing tube |
| 27 | electrode casing tube |
| 28 | active contact |
| 29 | return contact |
| 30 | offset |
| 31 | insulator |
| 32 | proximal portion |
| 33 | distal portion |

The invention claimed is:

1. An electrode instrument for a resectoscope, the electrode instrument comprising an electrode at a distal end and being able to be releasably coupled at a proximal end to a working element of the resectoscope via an electrical contact,
wherein two electrode casing tubes run from the electrode to the proximal end, and a first of the two electrode casing tubes comprises an active contact, and a second of the two electrode casing tubes comprises a return contact, and
wherein proximal portions of the two electrode casing tubes have a rectilinear configuration along a length of at least 24 mm, and/or distal portions of the two electrode casing tubes have a rectilinear configuration along a length of at least 100 mm.

2. The electrode instrument as claimed in claim 1, wherein the active contact is arranged electrically insulated inside the first of the two electrode casing tubes, and
the return contact is formed by an outer surface of the second of the two electrode casing tubes or is conductively connected to the outer surface of the second of the two electrode casing tubes.

3. The electrode instrument as claimed in claim 1,
wherein the active contact protrudes from the first of the two electrode casing tubes at the proximal end.

4. The electrode instrument as claimed in claim 1, wherein at least distal and proximal portions of the two electrode casing tubes run parallel to each other.

5. The electrode instrument as claimed in claim 1,
wherein longitudinal axes of proximal and distal portions of the first of the two electrode casing tubes lie in a common first plane, and longitudinal axes of proximal and distal portions of the second of the two electrode casing tubes lie in a common second plane, and
wherein the first plane and the second plane are oriented parallel to each other and such that a distance between the electrode casing tubes is identical along their entire lengths.

6. The electrode instrument as claimed in claim 1, wherein distal longitudinal axes of distal portions of the two electrode casing tubes each have at least one offset in relation to proximal longitudinal axes of proximal portions of the electrode casing tubes.

7. The electrode instrument as claimed in claim 6, wherein the offset has a distance of 2.5 mm to 3.5 mm.

8. The electrode instrument as claimed in claim 6, wherein the offset is S-shaped along a length of at most 30 mm.

9. The electrode instrument as claimed in claim 1, wherein a distance between the two electrode casing tubes in a proximal region measures 5.4 mm to 5.8 mm, and/or a distance between the two electrode casing tubes in a distal region measures 5.4 mm to 5.8 mm.

10. The electrode instrument as claimed in claim 1,
wherein a diameter of the two electrode casing tubes measures 1 mm to 1.4 mm, and
wherein cross-sections of the two electrode casing tubes are circular or ring-like along an entire length of the two electrode casing tubes.

11. The electrode instrument as claimed in claim 1, wherein the electrode, in a proximal region, is located within an extended, enveloping cylinder face of the two electrode casing tubes and does not protrude radially beyond the cylinder face of the two electrode casing tubes.

12. The electrode instrument as claimed in claim 1, wherein the two electrode casing tubes are connected via a first guide element in a distal portion and a second guide element in a proximal portion.

13. The resectoscope having the electrode instrument as claimed in claim 1.

* * * * *